US011318307B2

(12) United States Patent
Kern et al.

(10) Patent No.: US 11,318,307 B2
(45) Date of Patent: May 3, 2022

(54) FINGERTIP MOUNTED MICROCURRENT DEVICE FOR SKIN

(71) Applicant: NSE Products, Inc., Provo, UT (US)

(72) Inventors: Dale G. Kern, Hyde Park, UT (US); Richard R. Best, Mapleton, UT (US); Toan Doan, Orem, UT (US)

(73) Assignee: NSE Products, Inc., Provo, UT (US)

( * ) Notice: Subject to any disclaimer, the term of this patent is extended or adjusted under 35 U.S.C. 154(b) by 30 days.

(21) Appl. No.: 16/770,159

(22) PCT Filed: Jan. 3, 2019

(86) PCT No.: PCT/US2019/012219
§ 371 (c)(1),
(2) Date: Jun. 5, 2020

(87) PCT Pub. No.: WO2019/136176
PCT Pub. Date: Jul. 11, 2019

(65) Prior Publication Data
US 2021/0162212 A1    Jun. 3, 2021

Related U.S. Application Data

(60) Provisional application No. 62/613,330, filed on Jan. 3, 2018.

(51) Int. Cl.
*A61N 1/36* (2006.01)
*A61B 5/01* (2006.01)
(Continued)

(52) U.S. Cl.
CPC ............ *A61N 1/36031* (2017.08); *A61B 5/01* (2013.01); *A61B 5/0531* (2013.01); *A61B 5/443* (2013.01); *A61N 1/0456* (2013.01); *A61N 1/0472* (2013.01)

(58) Field of Classification Search
CPC .............. A61N 1/36031; A61N 1/0456; A61N 1/0472; A61N 1/328; A61N 1/36014;
(Continued)

(56) References Cited

U.S. PATENT DOCUMENTS

| 6,452,584 B1 | 9/2002 | Walker et al. |
| 6,840,955 B2 | 1/2005 | Ein |

(Continued)

FOREIGN PATENT DOCUMENTS

| JP | 1626995 | 2/2019 |
| KR | 101068809 B1 | 10/2011 |

(Continued)

OTHER PUBLICATIONS

Extended European Search Report dated Aug. 20, 2021 in connection with European Patent Application No. 19735783.3, 9 pages.
(Continued)

*Primary Examiner* — Amanda K Hulbert
*Assistant Examiner* — Natasha Patel
(74) *Attorney, Agent, or Firm* — Dorsey & Whitney LLP

(57) ABSTRACT

A device for delivery of TENS current or electrostimulation has a first skin contact electrode mounted on a first non-conductive fingertip base and having at least one contact area for current-bearing contact with skin and a connection to a TENS current source and has a second skin contact electrode, mounted on a non-conductive fingertip base that is the same as the first non-conductive fingertip base or is a second non-conductive fingertip base and having at least one contact area for current-bearing contact with skin and a connection to TENS current source. A control and power unit that supplies TENS current to flow through skin contacting and positioned between the first and second electrodes, and enables selecting the level of the current or energy supplied.

20 Claims, 16 Drawing Sheets

(51) Int. Cl.
*A61B 5/0531* (2021.01)
*A61B 5/00* (2006.01)
*A61N 1/04* (2006.01)

(58) Field of Classification Search
CPC ...... A61N 1/0484; A61B 5/01; A61B 5/0531; A61B 5/443
See application file for complete search history.

(56) References Cited

U.S. PATENT DOCUMENTS

| | | | |
|---|---|---|---|
| 8,165,685 | B1 | 4/2012 | Knutson et al. |
| 8,560,080 | B2 | 10/2013 | Singal et al. |
| 8,639,361 | B2 | 1/2014 | Nathanson |
| 9,205,254 | B1 | 12/2015 | Britt et al. |
| 9,254,395 | B1 | 2/2016 | Shambayati |
| D752,235 | S | 3/2016 | Levi et al. |
| 9,474,898 | B2 | 10/2016 | Gozani et al. |
| D810,312 | S | 2/2018 | Cascini et al. |
| D828,570 | S | 9/2018 | Boaz et al. |
| D847,359 | S | 4/2019 | Kern et al. |
| 2008/0312579 | A1* | 12/2008 | Chang .................. A61N 1/0424 604/20 |
| 2011/0224743 | A1 | 9/2011 | Britt |
| 2015/0321000 | A1* | 11/2015 | Rosenbluth .............. A61N 1/18 607/48 |
| 2016/0045678 | A1* | 2/2016 | Vallero ................ A61N 1/0484 601/46 |
| 2016/0303364 | A1 | 10/2016 | Osborne |

FOREIGN PATENT DOCUMENTS

| | | |
|---|---|---|
| WO | 2017053847 A1 | 3/2017 |
| WO | 2019136176 A1 | 7/2019 |

OTHER PUBLICATIONS

International Search Report and Written Opinion for PCT/US19/12219, dated Apr. 19, 2019, 14 pages.

* cited by examiner

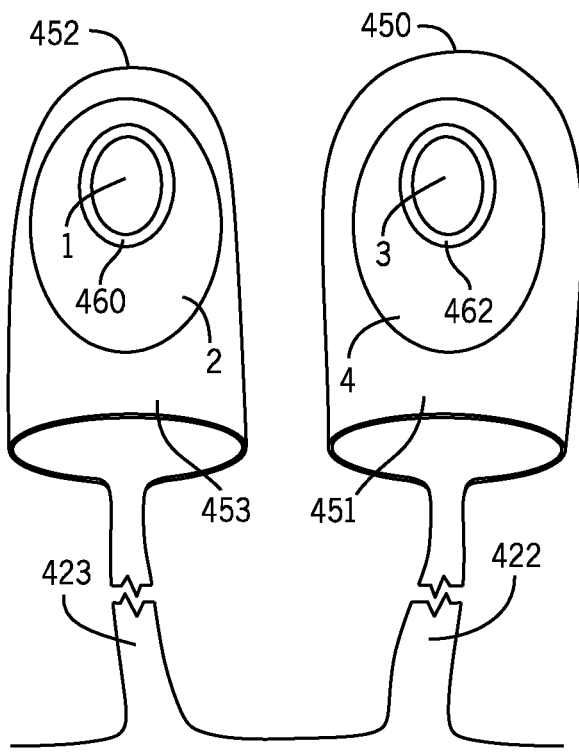
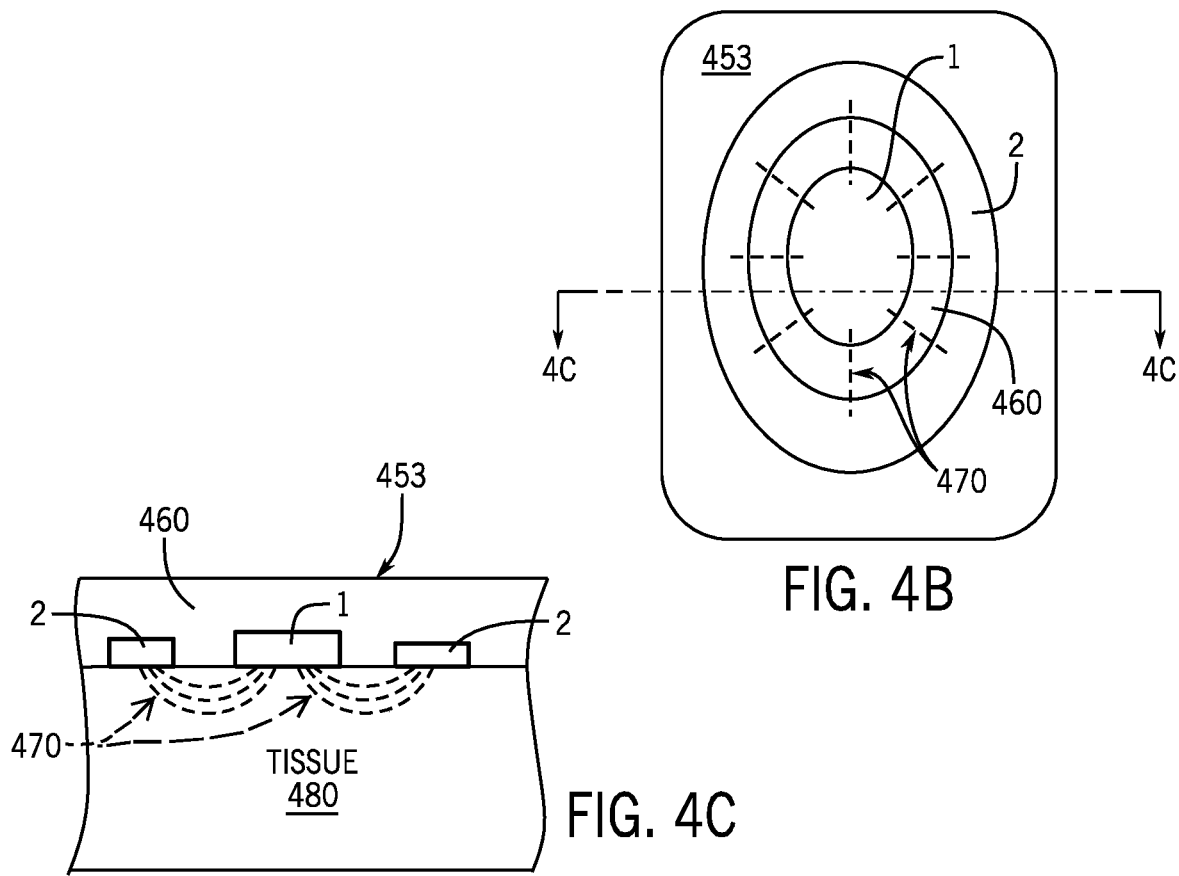

FINGERTIP MOUNTED MICROCURRENT DEVICE FOR SKIN

CROSS-REFERENCE TO RELATED APPLICATION

This application claims priority to U.S. Provisional Application No. 62/613,330, filed Jan. 3, 2018 and entitled "FINGERTIP MOUNTED MICROCURRENT DEVICE FOR SKIN," the entirety of which is hereby incorporated by reference for all purposes.

TECHNICAL FIELD

The invention relates to devices for treating skin, particularly facial skin, and an arrangement for delivery of microcurrents, such as TENS (Transcutaneous electrical nerve stimulation), to skin with electrodes mounted at the fingertips.

BACKGROUND

Skin is the largest organ of the human body, with several important functions, including forming a physical barrier to the environment, protection against micro-organisms, allowing and limiting the inward and outward passage of water and electrolytes, ultraviolent radiation and toxic agents. Within the skin there are three structural layers: the epidermis, the dermis and the subcutis. Keratinocytes are the main cell type found within the epidermis. Fibroblasts are the predominant cell type within the dermis. The dermis is composed of a supportive extracellular matrix and contains bundles of collagen which run parallel to the skin surface. The role of fibroblasts within the dermis is to produce collagen, elastin, and structural proteoglycans. The collagen fibers constitute 70% of the dermis, giving it strength and toughness, while elastin provides normal elasticity and flexibility. The proteoglycans provide viscosity and hydration. Transforming growth factor β (TGF-β) is associated with the regulation of extracellular matrix production in human skin connective tissue. Skin also is innervated and vascularized, and also contains small numbers of immune cells (e.g. mast cells, tissue macrophages, etc.).

Aging of human skin is associated with discoloration, wrinkling, and the sagging effect. These developments related to aging are dramatically visible in human skin, which becomes dry, wrinkled, lax, and irregularly pigmented over time. Typically, aged skin is characterized by a flattening of the dermal-epidermal junction, increased atrophy, and a loss of elasticity of the dermal connective tissue. The loss of firmness and elasticity is commonly associated with the decrease/loss and disorganization of the major extracellular components, including collagen I (associated with being the primary cause of wrinkle formation), elastin, and large and small proteoglycans and glycosaminoglycans. Aging skin also possesses decreased TGF-β, which results in reduced production of collagen and compromised wound healing. A histological analysis of aging in human skin has revealed a decrease in tissue thickness, disorganization of collagen, and accumulation of non-functional elastin.

Handheld devices are used for cosmetic purposes to deliver galvanic and TENS treatment to facial skin. Such devices have at least one electrical contact surface or electrode for placement against the skin to be treated and a second electrode for contact somewhere on the body to provide a complete circuit. Examples of such devices include those shown in U.S. Pat. Nos. 6,766,199, 7,305,269. 8,655,448, and 9,042,993 and US Publication Nos. 2015/0005681 and 2015/0360024.

There exist TENS products that have been approved by the U.S. Food & Drug Administration for aesthetic skin application purposes, such as the Facial Spa from Nu Skin, Rejuvenique Model #RJV10 from Salton, Inc.; Facial Toning System from Face Master; Nutritone from Isomera; and Trinity from Carol Cole—NuFace.

Skin to which a user wishes to provide aesthetic TENS (or other microcurrent) treatment is often on the face, which has multiple contours and small areas to which the user may wish to apply treatment. Accordingly, it can be difficult for a user to apply a larger skin contact electrode as found in some prior devices to the desired treatment area. In the absence of full contact of a treatment electrode with the desired treatment area, the electrical stimulation may be less than desirable or the desired current flux may not be delivered specifically to the area to be treated.

Appropriate TENS current and/or voltage is a matter of both user comfort and treatment effectiveness. A device that allows the user to select treatment parameters and/or that is able to sense skin attributes and use intelligent analysis to recommend or set, or allow a user to select, treatment parameters would be desirable.

SUMMARY

Disclosed herein is a device for delivery of TENS current. The device is attached to at least one fingertip and the associated hand. An electrode or conductive skin contact attached at at least one fingertip is used for delivery to skin of a TENS signal, as a current and/or voltage (and resulting power level), established between two electrodes. The device has an energy source for supply of electrical current, a control unit for receiving power and converting it into a desired electrical current waveform in a signal generation circuit connected to the energy source, for producing as an output the TENS signal for delivery to skin via electrodes or contacts for fingertip placement by the user. The control unit may also receive sensor inputs and process these inputs to determine recommended TENS treatment parameters or receive user inputs to select among available treatment parameters.

The device enables a user to apply TENS to a small treatment area, and also accommodates a user who wants to use TENS treatment on a larger area. The device described below shows in one or more embodiments how a TENS treatment may be delivered from skin contact electrodes placed on a fingertip or fingertips, and how these contacts allow application of TENS to a small area or to a larger or wider targeted treatment area. Moreover, placing the electrodes for TENS delivery on a fingertip allows a user to locate the electrode by fingertip feel, somewhat similar to a normal fingertip touch and to apply more or less pressure on the electrode contacting area, according to user preference, and again similar to a normal fingertip touch.

In various embodiments, the device delivers electrostimulation using (a) a first skin contact electrode, said skin contact electrode mounted on a first non-conductive fingertip base and comprising at least one contact area for current-bearing contact with skin and a connection to a TENS current source; (b) a second skin contact electrode, said skin contact electrode mounted on a non-conductive fingertip base that is the same as the first non-conductive fingertip base or is a second non-conductive fingertip base and comprising at least one contact area for current-bearing contact with skin and a connection to TENS current source: and (c) a control and power unit for supplying TENS current to flow through skin that contacts and is positioned between the first and second electrodes, and for selecting the level of the current or energy supplied.

In one embodiment, the skin treatment device has a control and power unit that comprises a controllable signal generator in the control and power unit for selecting an electrostimulation signal for delivery to a circuit comprising a skin area contacted by each of the first and second fingertip skin contact electrodes.

Also disclosed herein is a skin treatment method using the above device.

Additional advantages and novel features of the device will be set forth in part in the description that follows.

BRIEF DESCRIPTION OF THE DRAWINGS

FIG. 4A shows a schematic view of one embodiment of skin contact electrodes at two fingertip caps or elements of the device as shown in FIGS. 1, 2A-2B and 3A-3C, where each fingertip cap or element has two electrode areas, where one encircles the other and they are separated by non-conductive material.

FIGS. 4B-4C show enlarged, schematic plan and cross-section (respectively) views of skin contact electrode pair 1, 2 as in FIG. 4A at one fingertip base 453 and the flow of current (indicated by dotted lines 470) in skin tissue in contact with the electrode pair and in the skin tissue adjacent to and between the electrodes of the pair 1, 2 that is adjacent the non-conductive area 460.

DETAILED DESCRIPTION

Figure 1:
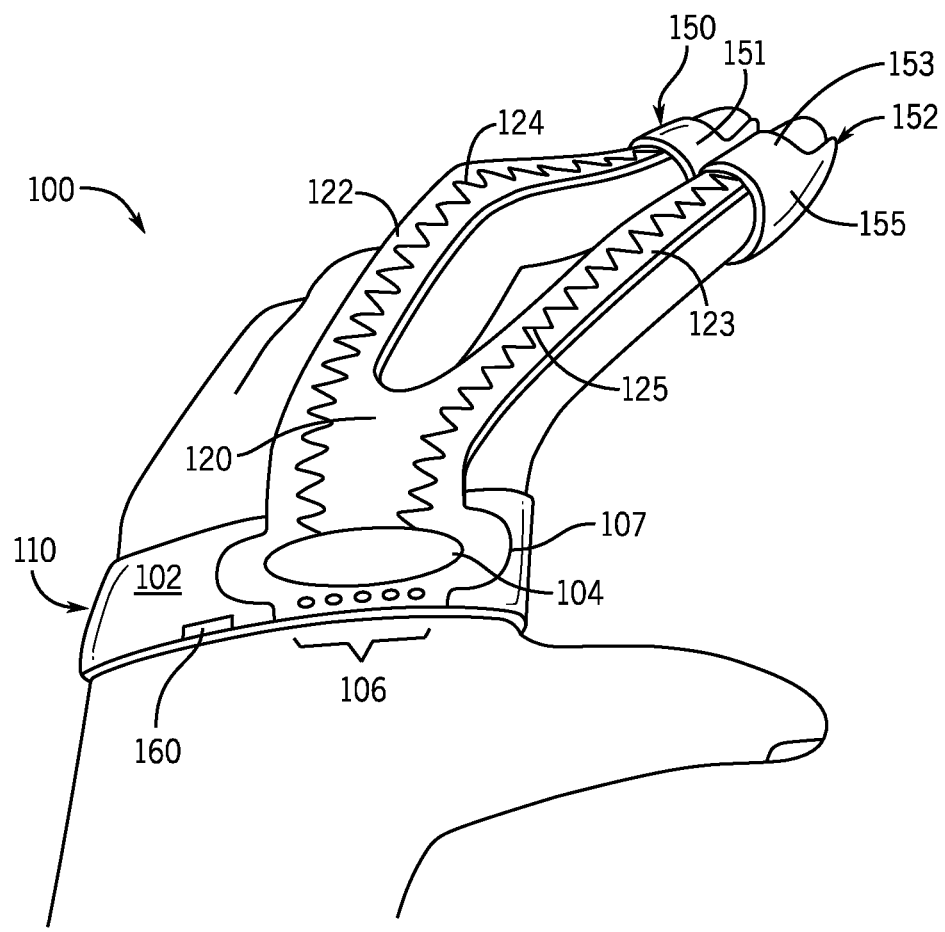
FIG. 1 is a pictorial view of a TENS device with a first and a second fingertip cap or element, each with a non-conductive fingertip base bearing at least one skin contact electrode and configured for attachment at a first and a second fingertip. Each electrode is connected to a hand or wrist-mounted control and power unit of the device via a flexible link that include wires or other electrical conductors.

Although the present disclosure provides descriptions of preferred embodiments, persons skilled in the art will recognize that changes may be made in form and detail without departing from the spirit and scope of the invention. Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Definitions

As used herein, the term "TENS" means Transcutaneous Electrical Nerve Stimulation and refers to the use of various electrical waveforms, also called microcurrents, which are known for medical uses and which also have been approved to be applied to skin for aesthetic, cosmetic or other human use by the U.S. Food and Drug Administration (FDA). In the following, references to "TENS" shall include any microcurrents used for electrostimulation similar to known TENS currents and waveforms or for other electrostimulation found to have beneficial effects on skin.

As used herein, the term "about" modifying, for example, a current or voltage or other electrical quantity means a measured value of the quantity, subject to variation that can occur, for example, through typical measuring procedures or through differences in the components or in a user's skin or other physiology and with variations that do not meaningfully affect the overall TENS effects of the device disclosed.

As used herein, the word "substantially" modifying, for example, a comparative description of a waveform employed in the embodiments of the disclosure, refers to a variation in waveform characteristics that does not meaningfully affect the overall TENS effects of the device disclosed. In the case of reference to an area receiving treatment, "substantially" recognizes that the exact extent of current flow and the amount of current in skin tissue at various points in proximity to an electrode is difficult to measure at any point in the area and may vary based on the type of tissue involved.

Device Overview

Disclosed herein is a device for delivering TENs current to skin. The device may be called a wearable device, because it is suited to fit on a portion of the body, at least during use. Although it is unlikely to be worn continuously for many hours (e.g., in the manner of a watch), as will be explained below, the adaptation of the device to be placed or mounted on a hand for a treatment session and to follow finger motion of the wearer has benefits for the user, as further explained below.

FIG. 1 is a pictorial view of one exemplary embodiment of a hand-mounted device 100 for TENS delivery from skin contact electrodes configured for attachment at at least one, and preferably a first and a second, fingertip. Device 100 is shown in FIG. 1, wherein device 100 includes a control and power unit 110 that is integrated into, and attachable to a user's hand by, a band or clip 102. As shown, control and power unit 110 may span the back of a user's hand and/or wrap around the hand between the thumb and forefinger to at least partially cover the user's palm. In other embodiments, the user's wrist may be encircled, similar to a bracelet. The control and power unit includes a battery, replaceable or rechargeable, or other power source, both for providing the power for a TENS current and for powering microprocessors, display, sensors or other components or circuitry that receive inputs, perform logical operations and produce outputs that may include the TENS current and those that may drive displayed information. The control and power unit 110 may include one or more control buttons, e.g., the row of buttons 105 built into band 102, to provide inputs for controlling the device 100. These may include an on/off switch and other buttons for selecting or controlling treatment parameters, operational modes, communications to other devices or displayed information. The control and power component 110 also may include a screen 104 to display device status, one or more operating parameters or user messages and other information. All or a section of the screen may be touch sensitive, to allow inputs in place of or in addition to use of buttons 106.

At the tips of two fingers, in one embodiment the index finger and the adjacent finger, are fingertip caps or attachment elements 150, 152. Each of these comprises a non-conductive base portion 151, 153 configured to receive or fit onto a fingertip of the user and to sit comfortably and securely on each of two respective fingertips, in the example shown, the index finger and the finger adjacent. The fingertip caps or elements may be molded plastic, fabric or other elastic or flexible material, that is shaped to fit a fingertip, including accommodating various fingernail styles. For example, the fingertip caps or attachment elements 150, 152 may be like a thimble, with a closed end or (as shown) with an open end that allows a fingernail to project outward.

In one embodiment each fingertip base 151, 153 has mounted on it or embodied in it at least one skin contact or electrode (partially visible at 155 on base 153). (The phrase "mounted on" shall mean any form of attachment by which a fingertip base serves as a support for a skin contact or electrode/conductor.) The fingertip contact may be made of any conductive material, such as a conductive plastic or metal patch attached on the nonconductive material of a base 151, 153. Preferably, a skin electrode comprises at least one defined area of electrically conductive material near the fingertip and opposite the fingernail, approximately in the area that a user naturally uses when lightly touching an object or a face or other part or a body. The skin electrode may have a surface pattern for aesthetic reasons and which may also assist in the holding or distributing a lotion or gel, if used with the device. A fingertip base also may have two or more skin electrodes or contacts formed by separate conductive patches or areas.

Each fingertip base is physically and electrically connected to the control and power unit 110. As see in FIG. 1, a relatively thin, flexible material link 120, roughly V-shaped, made of a textile or an elastomeric material, with the bottom of the V joined to the control and power unit 110, has a leg 122, 123 extending out to each fingertip base 151, 152. Each leg 122, 123 includes at least one conductor, such as a thin wire or a conductive thread or threads 124, 125. Making the link 120 from an elastic material that is stretched when the bases 151, 153 are placed on their respective fingertip may assist in holding the bases 151, 153 in place. A primary purpose of the conductor(s) is to make an electrical connection to deliver a TENS signal to an electrode of one or both of the fingertip bases from the control and power unit 110. Other conductors built into or on a leg 122, 123 may serve as electrical connections used by the control and power unit 110 to communicate with or to power sensor elements (for sensing moisture, temperature, etc.) that may be located at a fingertip or anywhere else along the extent of one or both legs 122, 123 or on a portion of band 102 contacting with the back or palm side of a user's hand.

If the device is battery powered or requires wire-based communication, the control and power unit 110, may include a socket 160 for connection of a recharging cord or for communications, including a single socket, such as USB format, that can carry both power and signals. In some embodiments where the device is battery powered and rechargeable, a charge level sensor may be coupled to a display visible to a user, wherein the user is alerted to the status of the remaining battery power. In some embodiments, communications by the control and power unit 110 to separate devices (e.g., a mobile phone) may be by Bluetooth or other known protocol or means.

In some embodiments, the control and power unit 110 further houses a sound or vibration indicator 107 that beeps, vibrates, or otherwise notifies the user of one or more status conditions, such as that a particular increment of time has passed. For example, a timer that causes a beeping signal to sound every 15 seconds, or every 30 seconds, or some other interval when the device is turned "on" for treatment may be used to alert the user that she or he should start addressing a different area of the skin or has finished a timed session.

Figure 2A:
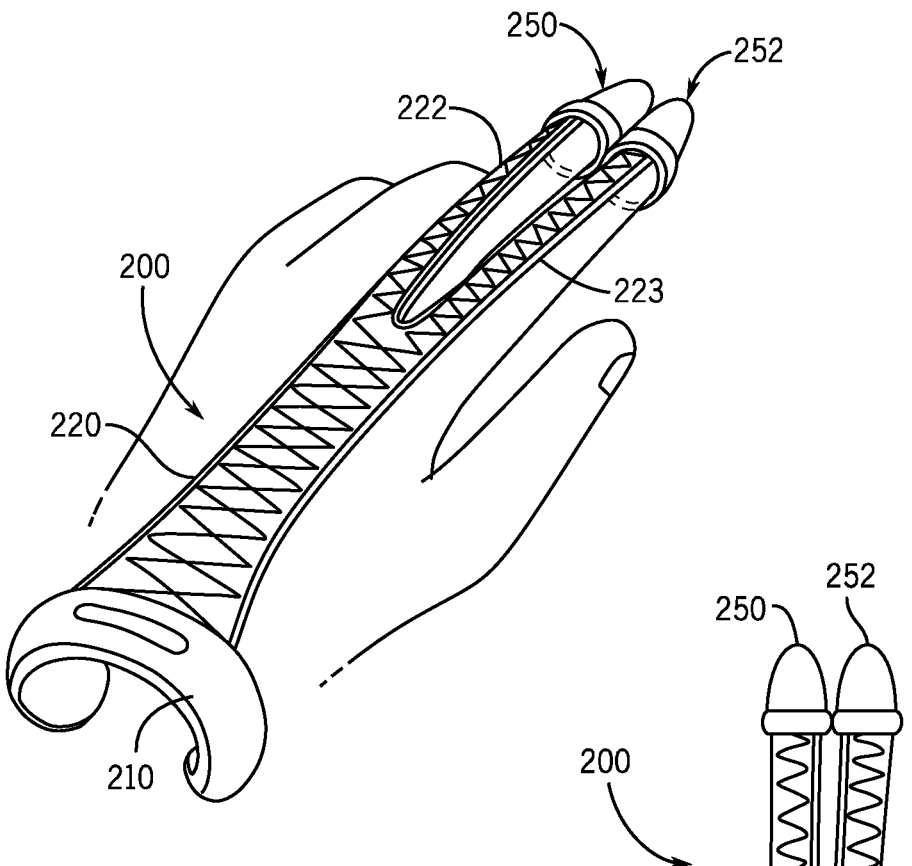
FIG. 2A is a pictorial view of another embodiment of a TENS device with a first and a second fingertip cap or element, each bearing at least one skin contact electrode and configured for attachment at a first and a second fingertip. Each electrode is connected to a hand or wrist-mounted control and power component of the device via a flexible link that include wires or other electrical conductors.
Figure 2B:
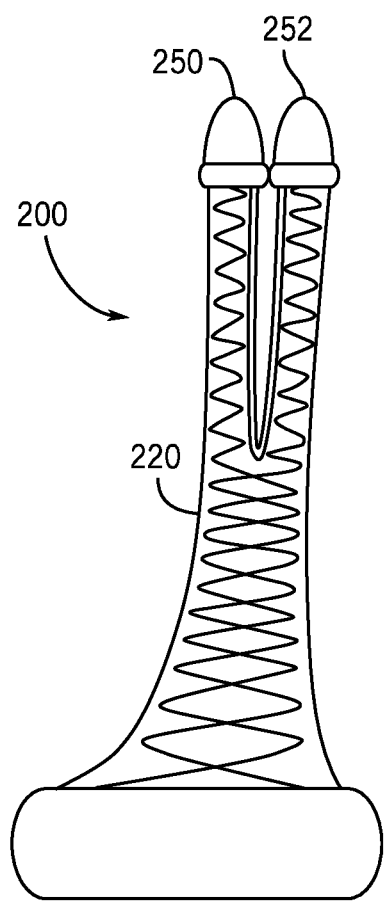
FIG. 2B shows in plan view the embodiment of a TENS device as in FIG. 2A, with a first and a second fingertip cap or element bearing at least one skin contact electrode for attachment at a first and a second fingertip, with each electrode being connected to a control and power unit of the device.

FIGS. 2A and 2B show an alternate embodiment of the device of FIG. 1. Here the device 200 has a control and power unit 210 that is wrist-mounted, more like a bracelet, and thus requiring a longer link 220 than shown in FIG. 1 to connect to fingertip caps or attachment elements 250, 252, each for supporting at least one electrode. As seen in FIGS. 2A and 2B, the link 220 may be made of a metal mesh or other conductive material, although if used to deliver TENS current to two electrodes the mesh portions would need to be configured with other non-conductive material to form two electrical connections configured to exclude or reduce current leakage into the user's skin on the back of the hand or fingers from current intended to reach fingertip-located TENS electrodes.

Figure 3B:
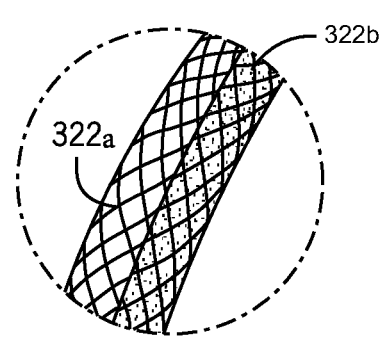
FIGS. 3A, 3B and 3C show a top view, a detail view and a side view, respectively, all pictorial, of another embodiment of a TENS device with a first and a second skin fingertip cap or element bearing at least one contact electrode for attachment at a first and a second fingertip. Each electrode is connected via a link to a control and power unit of the device partially positioned on the palm side of the hand.
Figure 3A:
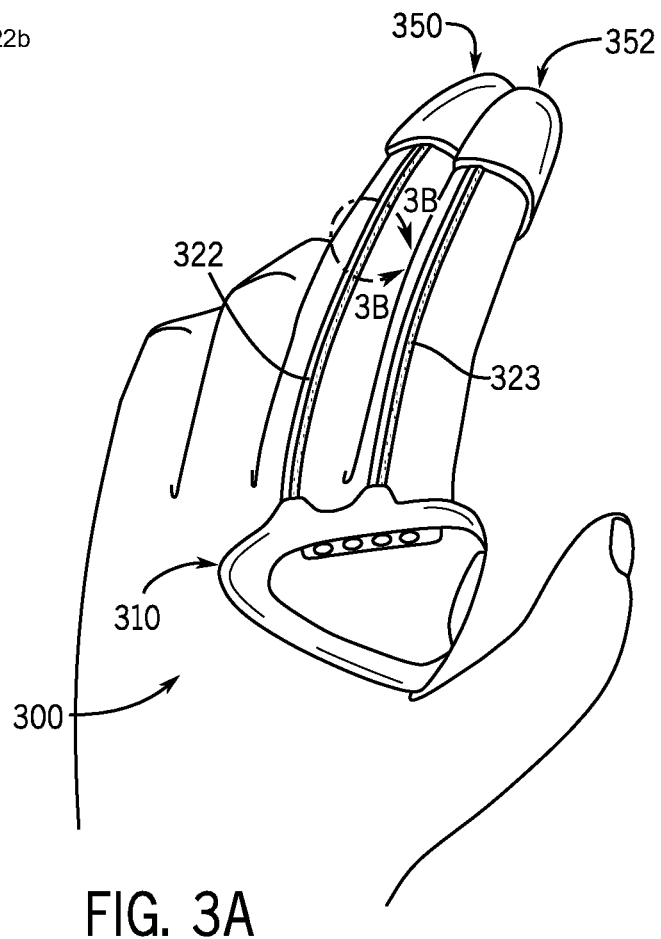
Figure 3C:
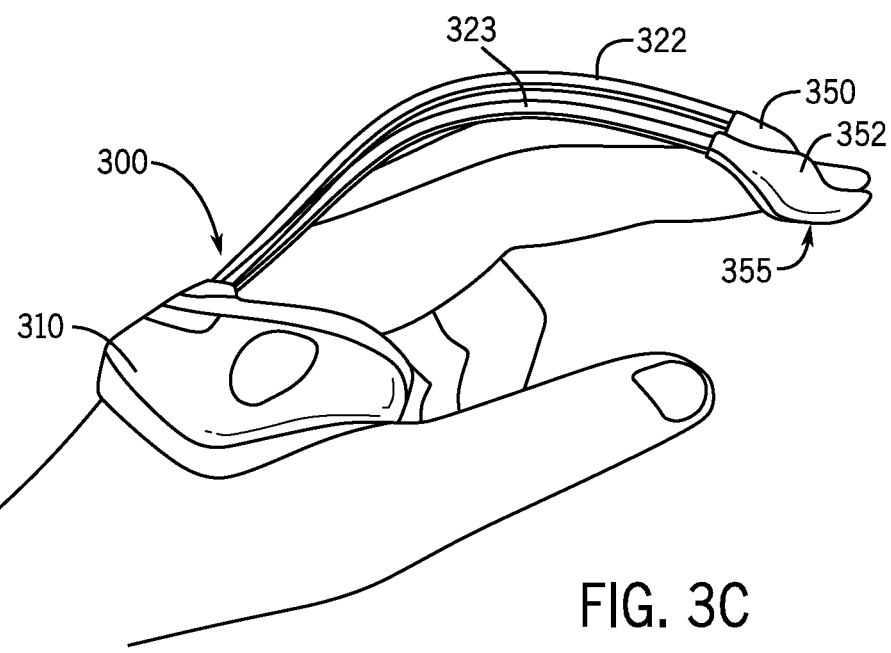

FIGS. 3A and 3B show a further embodiment of a fingertip-based TENS device 300. Here the device 300 has a control and power unit 310 more like a clip that fits over the back of the user's hand, on or near the first and second knuckles, and extends between thumb and forefinger to cover a portion of the user's palm, generally opposite the first and second knuckles. Here a shorter link may be used to connect to fingertip caps or attachment elements 350, 352. As seen in FIGS. 3A and 3B, the link may comprise a multi-conductor wire or flexible cable 322, 323 that extends along the back of each finger to connect to one of the fingertip caps or attachment elements 350, 352, each for supporting at least one electrode. In one embodiment, the conductive wire or cable 322, 323 associated with each at least one finger electrode may be made of a braided metal, such as copper or silver or other conductive material that can be braided and may offer aesthetic appeal, with or without use of its conductivity (which also may be performed by insulated wires made part of the braiding and electrically connected to at least one electrode). If used to deliver TENS current to two, paired electrodes at a fingertip (e.g., for treatment limited substantially to the skin contacting the single fingertip base, as in some embodiments described further below), the cables would need to be configured so that the legs 322, 323 of the link leading to the fingertip electrode pairs has at least two separate conductors connected to the control and power unit 310 to form two separate electrical connections, i.e., one complete circuit out to an electrode pair on each finger.

Figure 5A:
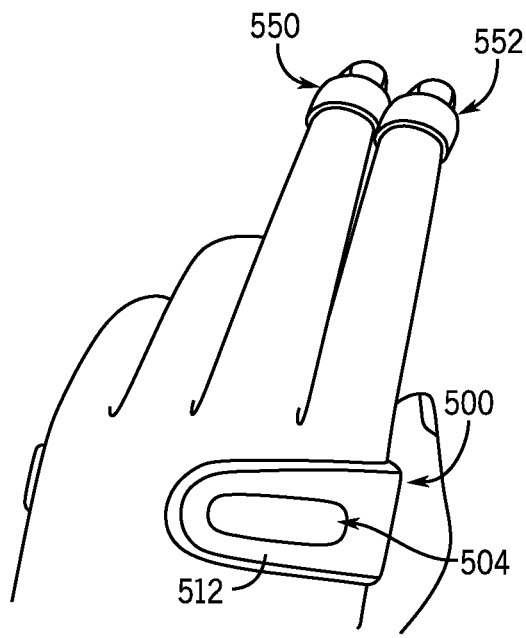
FIGS. 5A-5B show a top view and a bottom/side view, respectively, both pictorial, of another embodiment of a TENS device with a first and a second skin fingertip cap or element bearing at least one skin contact electrode for attachment at a first and a second fingertip. Each electrode is connected via a link positioned on the palm side of a finger to a control and power unit of the device, also partially positioned on the palm side of the hand.
Figure 5B:
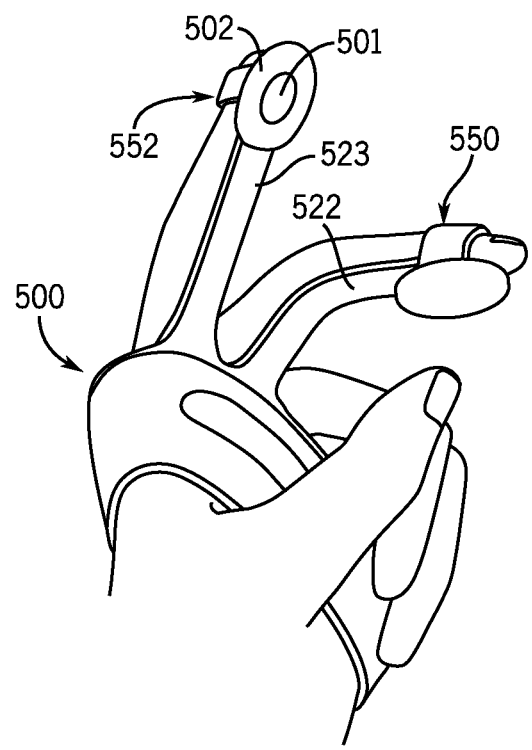

FIGS. 5A and 5B show a further embodiment of a fingertip-based TENS device 500. Here the device 500 has a control and power unit 512, again more like a clip that fits over the back of the user's hand, on or near first and second knuckles, and extends between thumb and forefinger to cover a portion of the user's palm. There the palm-located portion of the clip may extend across all or most of the width of the palm. In this embodiment, a link used to connect control and power unit 512 to fingertip caps or attachment elements 550, 552 is in the form of a pair of flexible links or legs 522, 523, extending from the portion of the control and power unit 512 located on the palm. The legs 522, 523 run on the interior or palm side of the associated finger. As seen in FIGS. 5A and 5B, each of legs 522, 523 may be a narrow strap or flexible strip that extends along the inside of each finger to one of the fingertip caps or attachment elements 550, 552. In one embodiment, the wire or other conductors associated with each finger may be a conductor (or conductor pair, if there is an electrode pair) embedded in the strap or flexible strip 522, 523. In one embodiment, the strap or flexible strip may be or include a resilient or springy material that would normally lie flat and generally straight but may be flexed when a finger is curled toward the palm. Upon such flexing, the strap or flexible strip 522, 523 stays against the inside of the associated finger. With a resilient material that changes a measurable quality upon deforming, it becomes possible to sense the amount of flexing of each finger, as further described below. Because the user controls the amount of finger flexing, the sensed degree of flexing becomes a possible user control input to the control and power unit 512, as discussed for controlling operational modes of the device.

Fingertip Base with Electrode Assembly

FIG. 4A is a simplified schematic view of two fingertip caps or attachment elements 450, 452, each comprising a fingertip base 451, 453 that may be placed on one of the first and second fingertips of a user of a device as shown in FIG. 1 and alternative embodiments. Leg 422 extends from the control unit (not shown in FIG. 4A) to base 451; similarly, leg 423 extends from the control unit to base 452.

Each fingertip cap or attachment element 450, 452 comprises a base portion 451, 453 configured like a thimble (although potentially with an open end) to receive or fit onto a fingertip of the user and to sit comfortably and securely on one of two fingertips. (The user's fingers do not appear in FIG. 4A.) Each base 451, 153 may be made of non-conductive, flexible material to serve as a foundation for electrodes 1, 2 on base 453 and electrodes 3, 4 on base 451. Electrode 1 on base 453 may comprise a circular or elliptical area or patch of conductive material 1 surrounded or encircled by a continuous strip of the nonconductive material 460, isolating electrode 1 from electrode 2. Electrode 2 comprises an outer, encircling annular or elliptical area of conductive material. Similarly, electrode 3 on base 451 may comprise a circular or elliptical area of conductive material surrounded or encircled by a continuous strip of the non-conductive material 462, isolating electrode 3 from electrode 4, which comprises an outer, encircling annular or elliptical area of conductive material. This is one format in which a fingertip base 451, 453 may support an electrode pair instead of just a single electrode. An electrode pair at one fingertip allows that fingertip to complete a TENS current circuit including the electrode pair and the small tissue gap between the areas where the two electrodes contact skin.

By contrast, when a fingertip base 451 or 453 supports only a single electrode (or, by control selection, only one electrode of multiple electrodes on a fingertip is electrically connected to the TENS current and thus active) then a second electrode, e.g., an electrode on the other finger, is used to form a circuit for the TENS signal. The circuit between these electrodes includes the tissue area located between the area at each fingertip where the single active electrode contacts skin. This results in a wider area receiving current than when only the electrode pair (1, 2 or 3, 4) at one fingertip is part of the TENS current circuit.

In embodiments with electrode pairs at both fingertips, at least one of, and in one embodiment, each of, electrode pair 1, 2 or pair 3, 4 may function in two modes. In one mode, electrodes 1, 2 on base 453 have different electrical potentials and are used to apply current that travels in the skin they contact and the skin between them, i.e., in skin that is adjacent the nonconductive area 460 in FIG. 4A. Similarly, operating in the same mode, electrodes 3, 4 on base 451 have different potentials and are used to apply current that travels in the skin they contact and the skin between them, i.e., in skin that is adjacent the nonconductive area 462 in FIG. 4A. FIGS. 4B and 4C show schematically and enlarged the electrode pair 1, 2 in a plan view (FIG. 4B) and in a view (FIG. 4C) taken at cross-section line 4C of FIG. 4B. In FIG. 4B, the TENS current (indicated by multiple, dashed lines 470) flows from electrode 1 to electrode 2 (or vice versa, depending on polarity) via the skin area that is between the skin area contacted by electrode 1 and that contacted by electrode 2. In FIG. 4C, the skin tissue area 480 in contact with electrodes 1 and 2 and in which the current (indicated by dotted lines 470) flows can be seen in cross-section. The current flow from electrode 3 to electrode 4 on the other fingertip base 451 (or vice versa, depending on polarity) follows the same pattern as explained for electrode pair 1, 2. As can be seen, the area into which and in which the current flows is small, being limited and focused on where skin is in contact with an electrode, with the spread of current into adjacent tissue being limited by the impedance of the skin and in general declining with distance from an electrode. Thus, while an electrode pair can be placed anywhere on an area to be treated, the area actually receiving available current is largely determined by the specific area contacted by the electrode pair and the narrow band of skin lying between these electrode contact areas through which current flows.

Figure 4D:
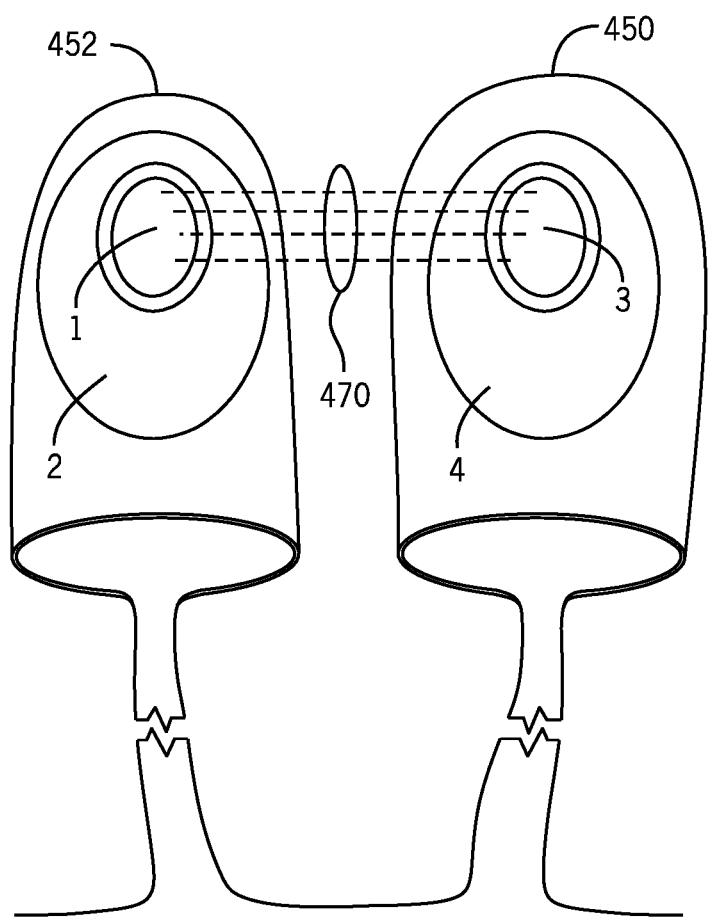
FIG. 4D shows a schematic view of how a pair of skin contact electrodes at each of first and second fingertip caps or elements 450, 452 of the device can operate with only the center or encircled electrode 1 or 3 delivering current into an area of skin in contact with the center or encircled electrodes 1, 3. This current (indicated by dotted lines) flows through a wider area of skin between the first and second fingertip caps, as opposed to just across the gap between electrodes 1, 2 or 3, 4.

In a second mode, a wider area can receive the TENS current, because each fingertip cap or attachment element 450, 452 uses a single electrode of its pair and the current must move between these. In the second mode, in one embodiment, only electrodes 1 and 3 are active and have electrical potential different from each other. Thus, electrodes 1, 3 are used together to apply current that travels from the skin contacted by electrode 1 to the skin contacted by electrode 3; the current (indicated by multiple, dashed lines 470) passes through the skin located between electrode 1 and electrode 3 (current indicated by multiple, dashed lines 470 in FIG. 4D). FIG. 4D shows in plan view this current flow. Thus, in this mode, the nonconductive areas 460 and 462 are not the main current path. Depending on where each of electrode 1 and electrode 3 is located by the user on skin to be treated, these contact areas 1, 3 define the ends of a wider area in which current flows. Thus, by moving a fingertip and the associated fingertip base 451 or 453 with its active contact, the user can define a larger treatment area located between the fingertip bases 451 and 453 to receive the TENS current than in the first mode.

Figure 4E:
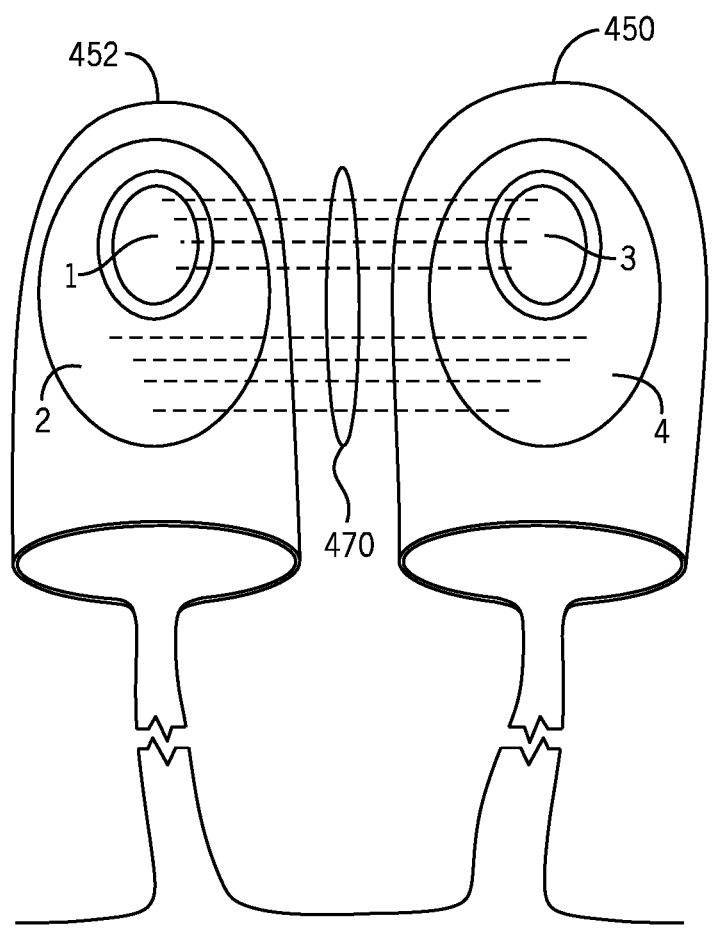
FIG. 4E. shows a schematic view of how a pair of skin contact electrodes at each of a first and second fingertip cap or attachment element 450, 452 of the device can operate at the same potential to deliver current to an area in contact with both electrodes in each of the electrode pairs 1, 2 or 3, 4. This current (indicated by dotted lines) flows through a wider area of skin between the first and second fingertip caps 450, 452.

In a third mode, a still wider area can receive the TENS current, because each electrode pair at a fingertip functions more like a single electrode. In the third mode as seen in FIG. 4E, electrodes 1, 2 have the same electrical potential but an electrical potential different from the electrical potential of electrodes 3, 4. Thus, electrodes 1, 2 are used together to apply current that travels between the skin electrode pair 1, 2 to the skin contacted by both of the second pair of electrodes 3, 4; the current passes through the skin located between electrode pair 1, 2 and electrode pair 3, 4 (indicated by multiple, dashed lines 470 in FIG. 4E). FIG. 4E shows in plan view this current flow. Thus, in this mode, the nonconductive areas 460 and 462 are not the main current path. Depending on where each of electrode pair 1, 2 and electrode pair 3, 4 is located by the user, these contact areas define the ends of a wide area in which current flows. Thus, by moving a fingertip cap or attachment element 450 or 452 with its respective contact pair, the user can define a larger treatment area located between the fingertip caps or attachment elements 450, 452 to receive the TENS current than in the first or second mode.

It should be noted that the second mode described above could be performed with electrodes 2 and 4 activated and encircled electrodes 1 and 3 inactive. This would be somewhat like the third mode but with a smaller area where current is introduced in the skin and where current flows out of the skin.

Figure 12A:
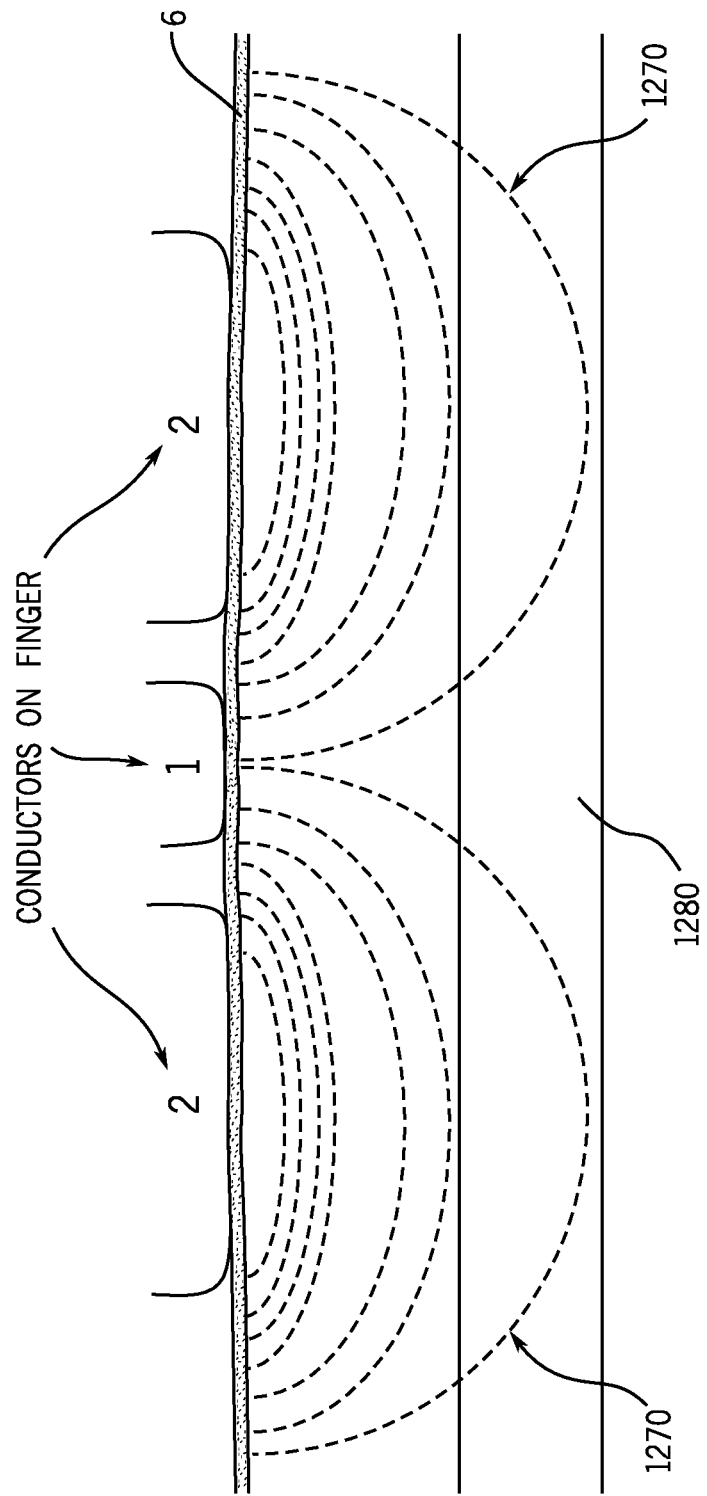
FIG. 12A shows an enlarged, schematic cross-section view of skin contact electrode pair 1, 2 as in FIG. 4A at one fingertip base and the flow of current (indicated by dotted and some parallel solid lines 1270) in skin tissue in contact with the electrode pair and in the skin tissue adjacent to and between the electrodes/conductors of the pair that is adjacent the non-conductive area.
Figure 12B:
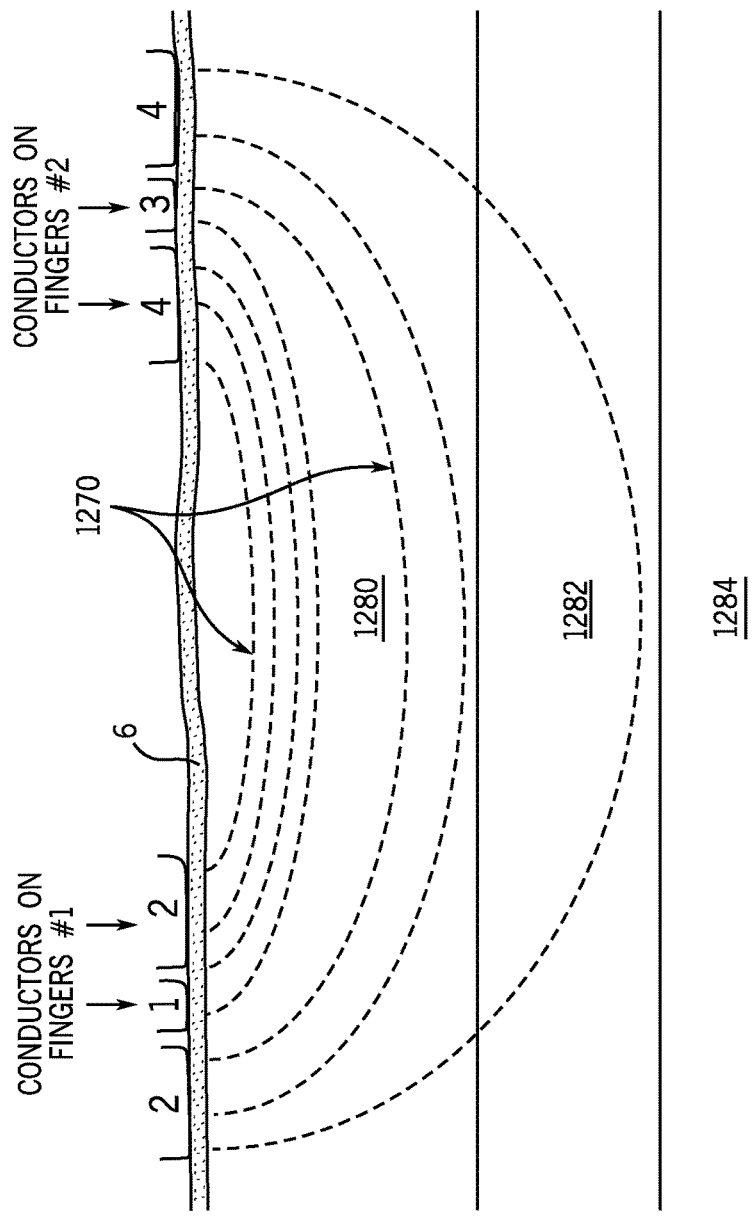
FIG. 12B shows an enlarged, schematic cross-section view of skin contact electrode pairs 1, 2 and 3, 4 as in FIG. 4A at two fingertip bases and the flow of current (indicated by dotted lines 1270) in skin tissue in contact with the respective electrode pairs and in the skin tissue adjacent to and between the electrodes/conductors of the separately positioned pairs.

FIGS. 12A and 12B show additional, alternative cross-sectional views of the current paths that will arise in the single fingertip, single active electrode pair mode (FIG. 12A) and the two fingertip, two active electrode pairs mode (FIG. 12B). Each of these FIGS. shows how a conductive gel 6 may be used at the skin surface and that the current in the tissue will be most dense on the paths that are the shortest paths between electrodes/conductors; however, lesser amounts of current may follow longer paths that "fringe out" from the electrodes/conductors and may pass through tissue at some distance from the electrodes/conductors. As seen in FIG. 12A, the current paths 1270 extend between electrodes/conductors 1, 2 of a single electrode/conductor pair through a layer of conductive gel 6 into the skin tissue 1280, with less current following longer paths that extend more deeply into the skin, away from the skin surface. As seen in FIG. 12B, the current paths 1270 extend between one pair of electrodes/conductors 1, 2 on one finger to a second pair of electrodes/conductors 3, 4 on a second finger, in each case through a layer of conductive gel 6 into the skin tissue 1280. With stronger currents and greater distance between the respective electrode pairs the current paths 1270 may extend into the extracellular matrix (ECM) tissue 1282 and into fat, vascular bed, muscle, bone and/or cartilage tissues 1284 at greater depths in the user's tissue adjacent the position of the electrodes as selected by the user. Again, depending on tissue types, it can be expected that there is less current following longer paths, which extend more deeply into the skin and into deeper tissue structures, away from the skin surface.

Control and Power Unit

Figure 9:
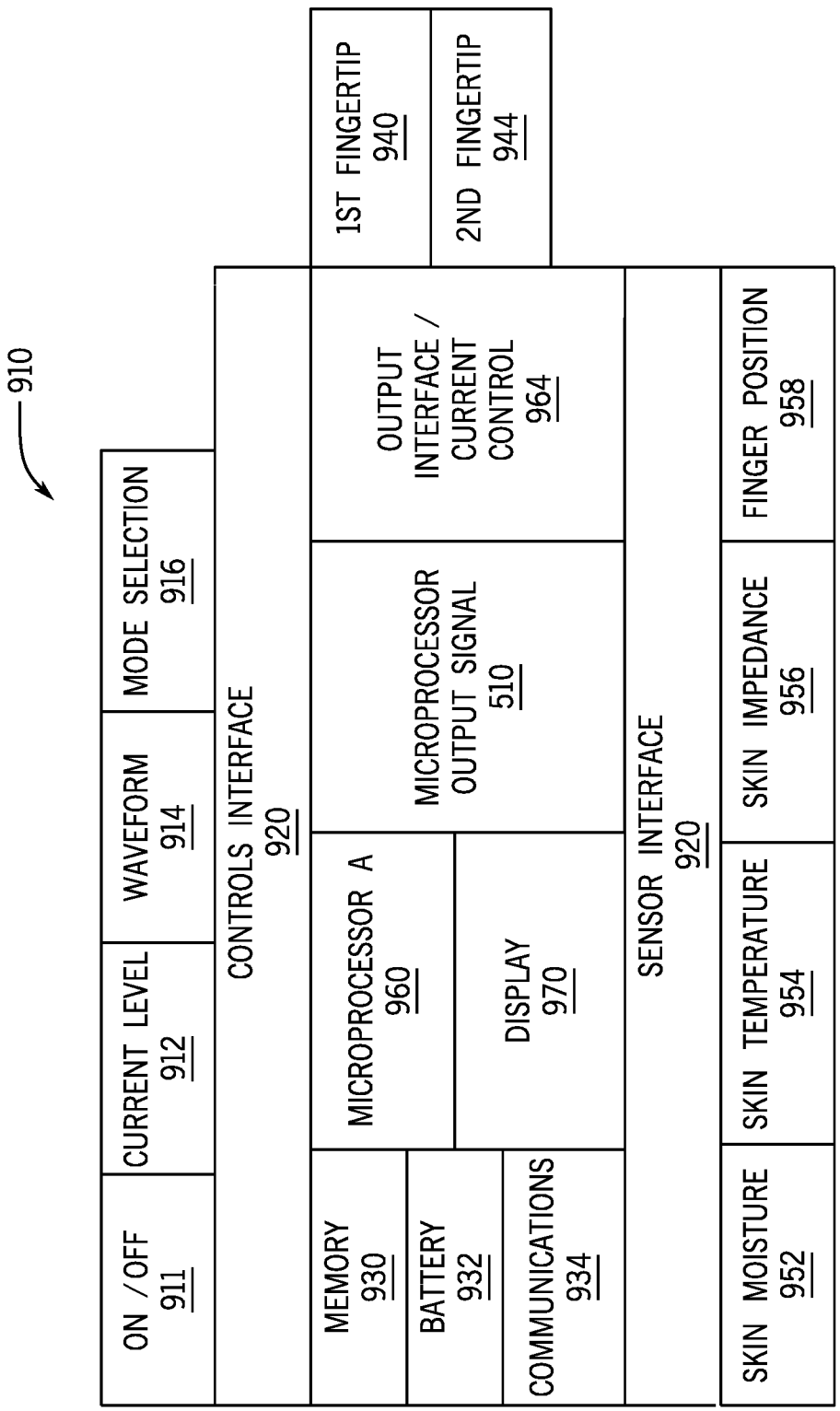
FIG. 9 shows a schematic block diagram of the control and power unit for controlling and producing the TENS output signal for embodiments of the present invention.

FIG. 9 shows a schematic block diagram of the control and power unit 910 for controlling and producing the TENS output signal for embodiments of the present invention. i.e., shows an embodiment for the control and power unit 110 of FIG. 1, 210 of FIGS. 2A, 2B, 310 of FIGS. 3A, 3B, or 512 of FIG. 5A. In general, the control and power unit 910 comprises multiple electrical components, including certain digital processing components, that determine the TENS current delivered in various operating modes and circumstances and provides the user control options and information.

The control and power unit 910 of FIG. 9 is powered by a battery 932 (replaceable or rechargeable) which may power all components, including main microprocessor 960 and output signal microprocessor 510. Memory 930 (which may be separate or integrated with microprocessor components) stores computer program instructions used by main microprocessor 960 and output signal microprocessor 510. The specific programming for the main microprocessor may vary according to the features desired, including the (a) specific sensors used, (b) the control features available (such as current/power level selection solely by user subject to a safety limit or current/power level based on sensor inputs and algorithms that select a current/power level commonly accepted to be comfortable and effective, but subject to user override), (c) offering the user session timers or use recommendations displayed on a display; (d) session recordkeeping and storage and or transmission of session data to another device; (e) status or error messages about the device; and (f) other features to inform and engage the user.

Communications component 934 serves to provide wireless (e.g., Bluetooth, Wi-Fi) or wired (e.g., via a regular of mini USB port) communications, such as to a phone or other personal digital device (not shown) that may have an application program allowing data and/or control signals to be exchanged between the phone or other personal digital device and the control and power unit 910. A display 970 may be driven by main microprocessor 960 (or other components with display drivers) to display menus, status or other device information. The display 910 may be touch sensitive, so that it also can be used to receive inputs by user touch or touch combined with motion or pressure.

To enable the user to interact directly with the control and power unit 910, the control and power unit 910 has a controls interface 920 that receives input signals from an on-off switch or similar input device 911; a current level selection input device 912, which may be a separate button or touch screen button defined on display 970; a waveform selection input device 914 and a mode selection input element 916 (e.g., electrode use modes discussed above for a small treatment area or wider treatment areas).

The control and power unit 910 also has a sensor interface 950 that receives input signals from one or more sensors, including (in some embodiments) a skin moisture sensor 952, a skin temperature sensor 954, a skin impedance sensor 956 and a finger flexing and/or position sensor 958. The data input by these sensors is collected and passed to various program modules executing in the main microprocessor 960, for processing of the sensor data as inputs to one or more control algorithms, including those involved in determining a recommended power level for the TENS to be delivered and monitoring current levels both for safety and for user comfort. For example, the control and power unit 910 can monitor the current level or the power level delivered from the output interface/current control module 964 and with limiter circuitry ensure that a specified current level or power level is not exceeded. The control and power unit 910 may be configured with a computer-based current recommendation module for taking as input one or more of a sensed value for impedance between first and second skin contact electrodes, skin moisture or skin temperature and providing as output a recommended output current from a controllable signal generator for providing a TENS signal for delivery to a circuit comprising a skin area contacted by each of the first and second skin contact electrodes with first and second electrical connections to the control and power unit.

Because user comfort appears to be related to the amount of current or power passing through an area or volume of tissue and the different operating modes discussed above involve different contact electrode surface areas (including larger or smaller areas) that are active for current or power delivery, the limiter circuitry or the settings for it in the microprocessors 960 or 510 may vary according to the operational mode selected. They may also vary in relation to a sensed distance between two fingertips, when two fingertips are used in a mode for treating a wider area. The user may place the fingertips and thus associated electrode surfaces close together or spaced by several inches, with greater spacing generally leading to increased impedance in the current path. Thus, in one embodiment, the TENS current and/or a limit values might be adjusted to reduce current when fingertip spacing is reduced.

Another approach to user comfort that may be used is that the control and power unit 910 of the device may be programmed to recommend an electrical output setting based on sensed inputs. The user could adjust the recommended setting level up or down within a range based on preferences and level of comfort through a separate button or touch screen button defined on display 970. In one example, the user might be able to adjust a recommended or base setting plus or minus a percentage, such as 10% or 20% of the base. However, the device would still have a maximum output setting that cannot be overridden.

Output signal microprocessor 510 and output interface/current control module 964 are used to define and to shape power from the battery 932 into the TENS signal to be delivered at first fingertip output 940 and second fingertip output 944, in each case with the currently ultimately being delivered via electrical connections from the outputs 940, 944 to the selected, active electrodes at one or both fingertips, depending on the modes of operation discussed above.

Sensors for sensing skin moisture 952 may be located on fingertip caps or attachment elements, such as those referenced as 150, 152 in FIG. 1. One type of sensor that may be used is based on near infrared spectroscopy. See "Correlation between near infrared spectroscopy and electrical techniques in measuring skin moisture content", M Mohamad et al 2014 J. Phys.: Conf. Ser. 546 012021. Capacitance or conductance based technologies may also be used to measure skin moisture. Other Information about available sensors for use in this context may be found at, among other sources:
https://www.karger.com/Article/Abstract/211353
http://www.google.com/patents/US5738107
https://www.sciencedaily.com/releases/2017/01/170130111030.htm
http://www.courage-khazaka.de/index/php/en/products/scientific/281-moisturemap
http://www.ieexplore.ieee.org/document/6504435/
https://www.macsphere.mcmaster.ca/bitsream/11375/14416/1/fulltext.pdf Sensors for sensing skin temperature 954 may also be located on fingertip caps or attachment elements, such as those referenced as 150, 152 in FIG. 1. Such sensing may be done with thermistors or with infrared radiance-based sensor technology Skin impedance between electrodes may best be measured by monitoring voltage and current flowing between the selected, active electrodes, but may also be measured by other sensors in contact with the tissue areas of interest. For example, it may be desired to determine impedance in certain tissue before any electrodes are active. Impedance may be automatically determined before each session. For example, the control and power unit 910 may send out DC test current pulses of short duration to the skin electrodes (or specialized impedance sensor electrodes) to determine the skin resistance. These current pulses may be as low in magnitude as 100 uA each pulse. For accuracy in determining the impedance, the control program for testing may define a short interval for each pulse or group of pulses to establish a stable reading. The control and power unit 910 can be programmed to take an average of values derived from the test pulses and to reject any false reading, such as from shorting the electrodes out or the user not putting the electrodes on the skin. When the reading using test pulses is finished, the control and power unit 910 may have an indication, such as a beep, light or displayed message, to let the user know the impedance reading has been established successfully, or an error indication if the reading has not been accomplished reliably or correctly. By this or similar means, the control and power unit selects the level of the TENS current or energy supplied in response to a sensed impedance between the first and second fingertip mountable skin contact electrodes. The impedance encountered can vary widely, in view of the freedom the user has to place the fingertip mountable skin contact electrodes on any skin area and (where two fingertips are active) with any separation distance the user's fingers and the device's link and leg structure on the fingers will allow. Variations in impedance can also arise due to skin moisture, the presence of lotions or creams and other physiological or user-effected conditions of the skin to be treated, Adapting to the impedance encountered, either by automatic action of a current-level setting algorithm fed sensor data and/or by enabling user selection of current level, allows user comfort to be achieved in the varying use conditions and modes the device makes possible.

The selection of an operational mode may be done with small button switches (e.g., buttons 106 in FIG. 1) located on the control and power unit or by use of menus displayed on display 970 and associated menu selection buttons that are mechanical or that are part of the display and touch sensitive. An alternative way for a user to provide input for mode selection may be based on deformation sensors that can be used to sense user finger position.

Figure 8C:
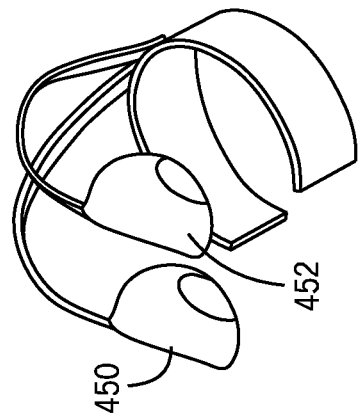
FIGS. 8A-8E show schematic diagrams of an embodiment of the TENS device that uses deformation sensors placed on the back or front of fingers or between them that allow bending or other positioning of fingers to be sensed, allowing this sensor input to be used for device control.
Figure 8B:
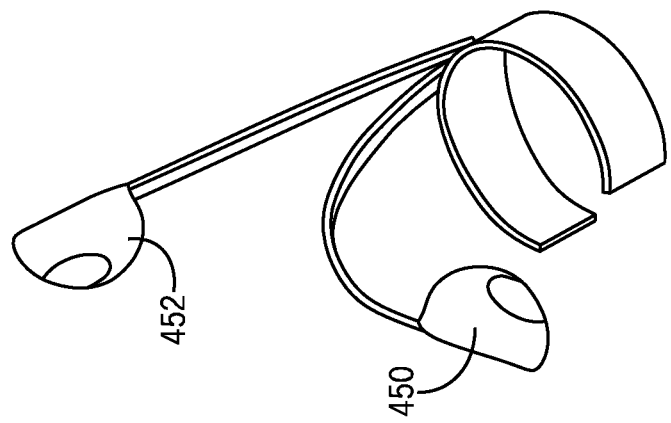
Figure 8A:
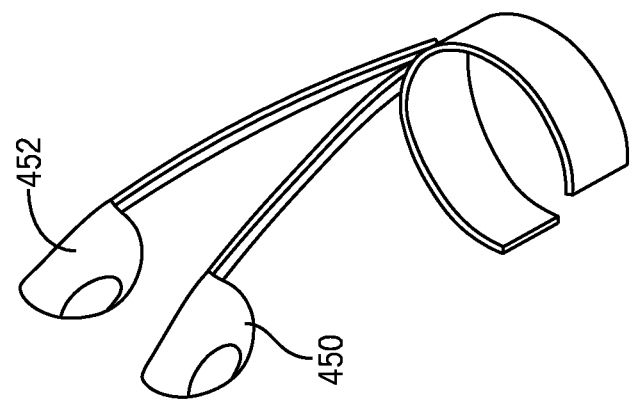

FIGS. 8A-8C show one method for how the user may control the use mode of the device. Various finger positions may be designated as associated with the available modes. For example, FIG. 8A shows that to do a wider area treatment a user wearing the device, such as the embodiment shown in FIGS. 5A-5B, the user may raise both fingers carrying a fingertip cap or attachment element (such as those referenced as 450, 452 in FIGS. 4A). This finger position, including an angle or degree of bending, can be recognized as selecting a mode in which the electrical current is delivered from contact pair 1 and 2 (both at the same electrical potential) on one fingertip, to contact pair 3 and 4 (both at the same electrical potential) on the second fingertip, but at an electrical potential different than contacts 1, 2). As shown in FIG. 8B, to select a local area treatment, the user may raise one finger, e.g., the fingertip cap or attachment 452 and fold the other finger with fingertip cap or attachment 450 down. When this finger positioning is recognized, the electrical power is then delivered only to the finger recognized as being raised. In a finger position as seen in FIG. 8B, the current flows only between the pair of contacts on the raised finger; if the other finger were raised, then the current flows only between the pair of contacts on that finger. In each case the treatment is to the small area touched by the contacts at one fingertip and the tissue between them. In one embodiment, either finger may define the treatment area, depending on which finger is raised. In one embodiment, with both fingers bent as in FIG. 8C, the unit is paused or turned off.

To implement the finger position method of setting of mode, at least two sensor approaches may be used. In method 1: Using flexible resistive sensors embedded in and along the fingertip links (e.g., 522, 523 in FIG. 5B), the position of the fingertip and/or finger, including an angle or degree of bending, and/or finger position in relation to the palm of the hand is determined. A flexible resistive sensor will change resistance when it is bent. This property can be utilized to sense the bending of fingers by monitoring the resistance change. Flexible resistive sensor technology from Spectra Symbol Corp. of Salt Lake City, Utah can be found at: http://www.spectrasymbol.com/wp-content/uploads/2016/12/FLEX-SENSOR-DATA-SHEET-v2014-Rev-A.pdf.

In method 2: As an alternative to the flexible resistive sensor technology another type of sensor available from Bend Labs, Inc. of Salt Lake City, Utah can be used to achieve the same operation modes. Bend Labs technology acts like an external neural network for measuring the complex ways body parts move. Bend Labs soft sensors can be configured to measure bending, stretching and pressure. This technology can be thus be used to sense and to measure the finger positions. Information on the technology can be found at:

http://www.bendlabs.com/technology.html and http://www.bendlabs.com.

Figure 8D:
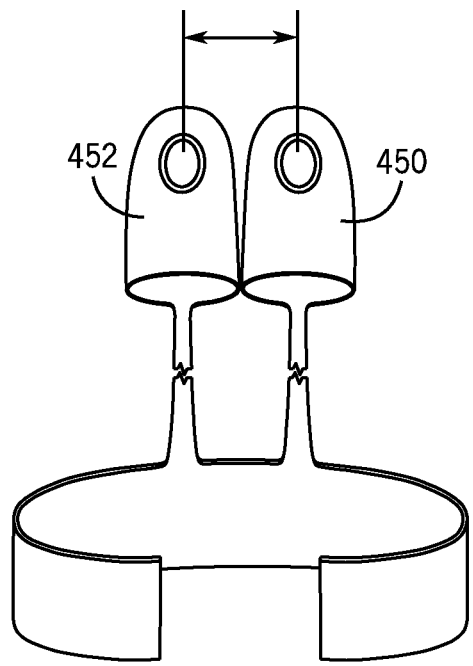
Figure 8E:
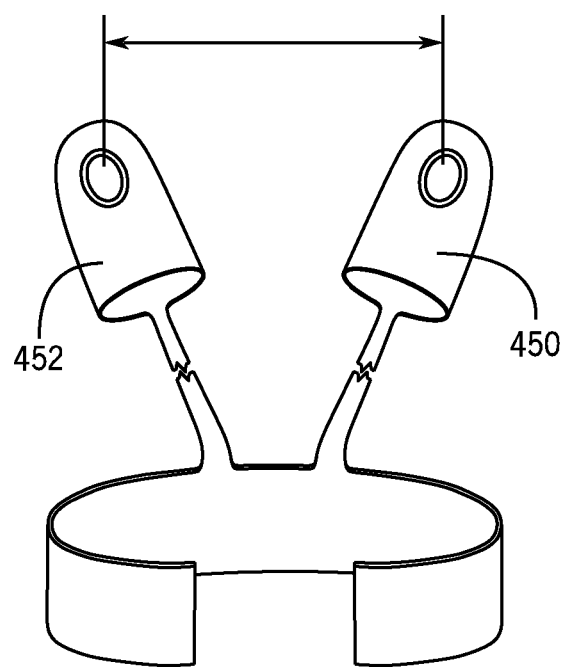

As a further, alternative way to allow a user to specify operational mode, the relative position of fingertips may be sensed. FIGS. 8D-8E shows that the fingertips can be moved together or apart when in use. Through stretchable sensors, the distance between the fingertips is estimated. Because the Bend Labs soft or stretchable sensors can be configured to measure bending or stretching, a small sensor can be placed between the fingers where they extend from the knuckles, i.e., at a position between the knuckles and opposite the fingertips, to measure how far the fingertips are spread apart. Increasing distance between the fingertips causes the sensor placed between the knuckles to stretch (deform) and this allows the device to measure how wide apart the fingertips are. Thus, the sensors provide inputs distinguishing the closely-spaced fingertips of FIG. 8D from the separated fingertips of FIG. 8E. As noted above, this distance measurement input may be used to increase or decrease an actual or recommended current value to reduce the chance of user discomfort from too high a current or power level.

Sensing the distance between fingertips allows to the device to adjust the electrostimulation output to optimize treatment based on the distance between the skin contacts placed on the area being treated. Another possible mechanism to achieve this is through constant monitoring of skin impedance changes measured at the area being treated. The electrical output will very proportionally based on the impedance changes throughout use. Sensing bending of a finger allows this bending to serve as a switch, for example between local area treatment (one finger bent) and wide area treatment (both fingers extended). Such sensing also allows the user to pause the treatment when both fingers are sensed as bent. The sensed finger positions may be interpreted by the control and power unit that receives the sensor data in any way that is programmed in design of the control and power unit.

Figure 6:
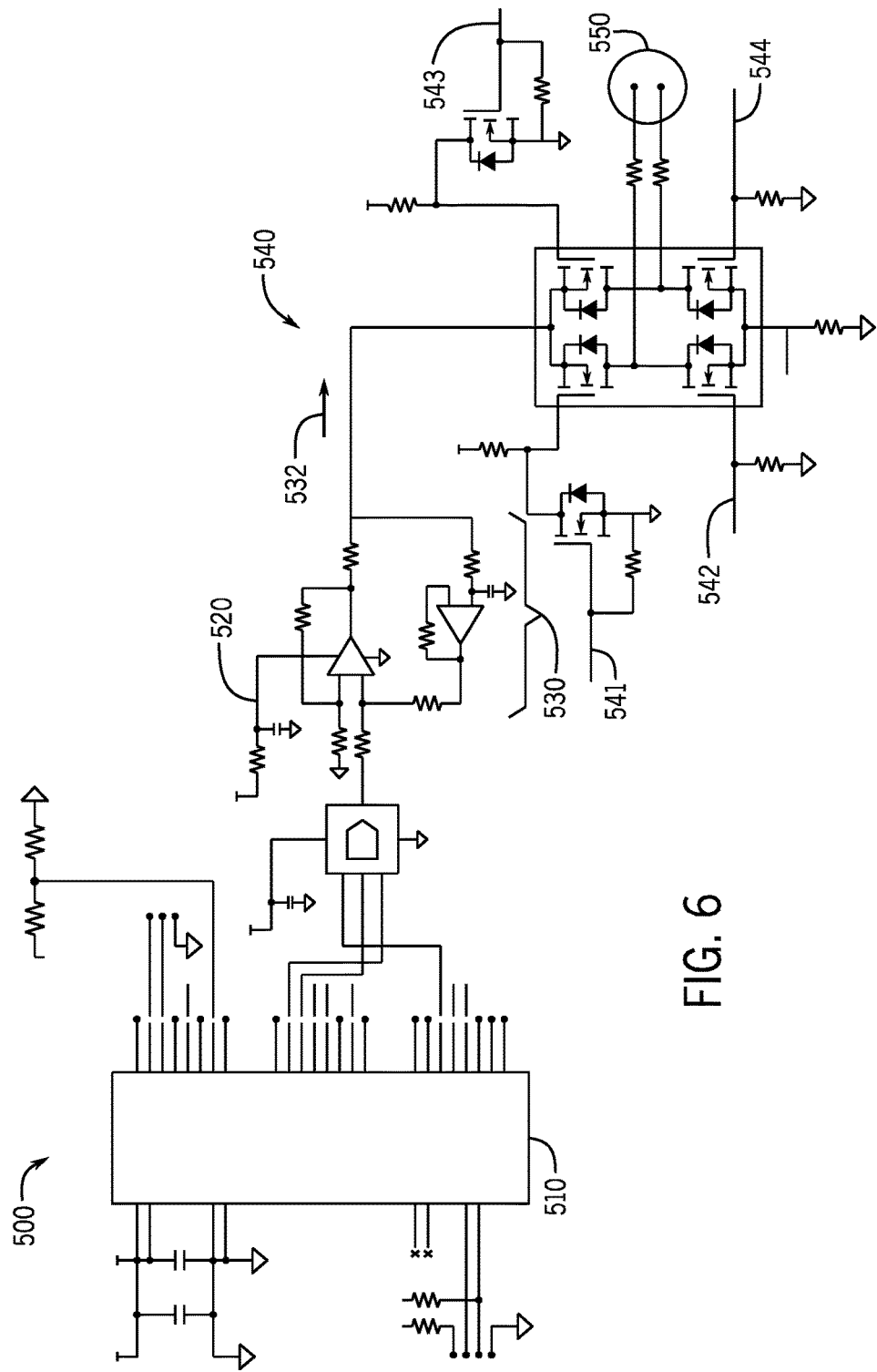
FIG. 6 shows a schematic circuit diagram of a TENS waveform generating circuit subassembly for use in the TENS delivery devices as shown in FIGS. 1-5.
Figure 10:
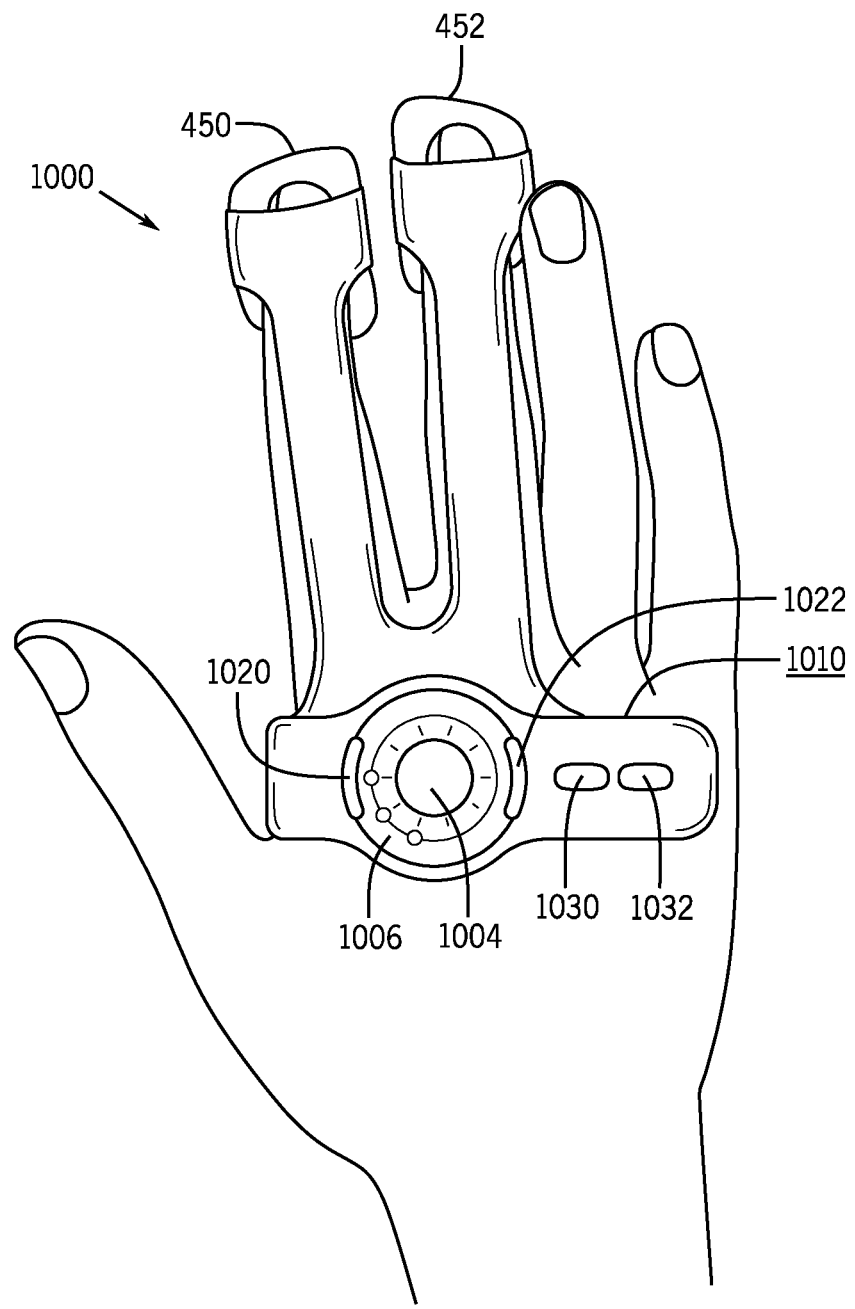
FIG. 10 is a pictorial top (back of hand) view of one embodiment of the device with a hand-mounted power and control unit that has control buttons and a display for power levels or other information.

FIG. 10 shows one embodiment of a TENS device 1000 of the kind described above, with two fingertip caps or attachment elements 450, 452, in which an embodiment of a user interface is shown. Here the user interface includes a display 1004 on which information, including selection menus, may be displayed. Button 1020 allows upward scrolling of a menu, while button 1022 allows downward scrolling. A circular array of indicator lights 1006 surrounding the central display area 1004 may show one or more recommended level current or power levels among those available. Button 1030 may be used to signal selection of a recommendation of current level or other option displayed. Button 1032 may be used to indicate a rejection of the recommended level or option and once a level or option has been selected and in use, it may be used to halt current. The display 1004 may show timers and a variety of status information TENS Waveform Generation Electronics Subassembly FIG. 6 shows a schematic circuit diagram 500 of the TENS waveform generating circuit subassembly of the components for generating the TENS output signals at outputs 940, 944 in FIG. 9. (See also description and depiction of this circuit in US Pub. No. 2018/0361137 A1, incorporated herein by reference.) At the left of FIG. 5 is an ultra-low power microprocessor 510 for signal generation timing, such as TEXAS Instruments MSP430. The microprocessor is configurable by programming or other means to determine one or more parameters of a TENS signal, to give the signal a waveform suitable for aesthetic TENS treatment, i.e., a waveform that the US FDA will view as acceptable in a 510 k application pointing to one or more aesthetic TENS waveforms of a predicate device previously approved in a 510 k application. Certain outputs of the microprocessor 510 are supplied to a digital to analog convertor (DAC) 520 and others to a precision current source circuit 530 based on two op amps. The current 532 from the precision current source circuit 530 is connected to a full bridge output circuit 540 for single ended signal phase reversal, i.e., it controls the polarity of the TENS output waveform, based on signals supplied by the microprocessor 510 at inputs 541, 542, 543, 544.

These various circuit elements permit a TENS output signal with the desired waveform, power level and the changing polarity as accepted by the FDA for aesthetic TENS application to be delivered at the output wire pair 550. Filings with the FDA for the Rejuvenique Model #RJV10 from Salton, Inc.; Facial Toning System from Face Master; Nutritone from Isomera; and Trinity from Carol Cole—NuFace, mentioned above, show several FDA-approved aesthetic TENS waveforms, which may be used substantially identically or in one or more variant forms in one or more embodiments of the present device. More specifically, the microprocessor 510 provides at four input points 541-544 to full bridge output circuit 540 signals that control and thus allow the specification of the timing, pulse duration and other parameters of the output waveform and its polarity.

Figure 7:
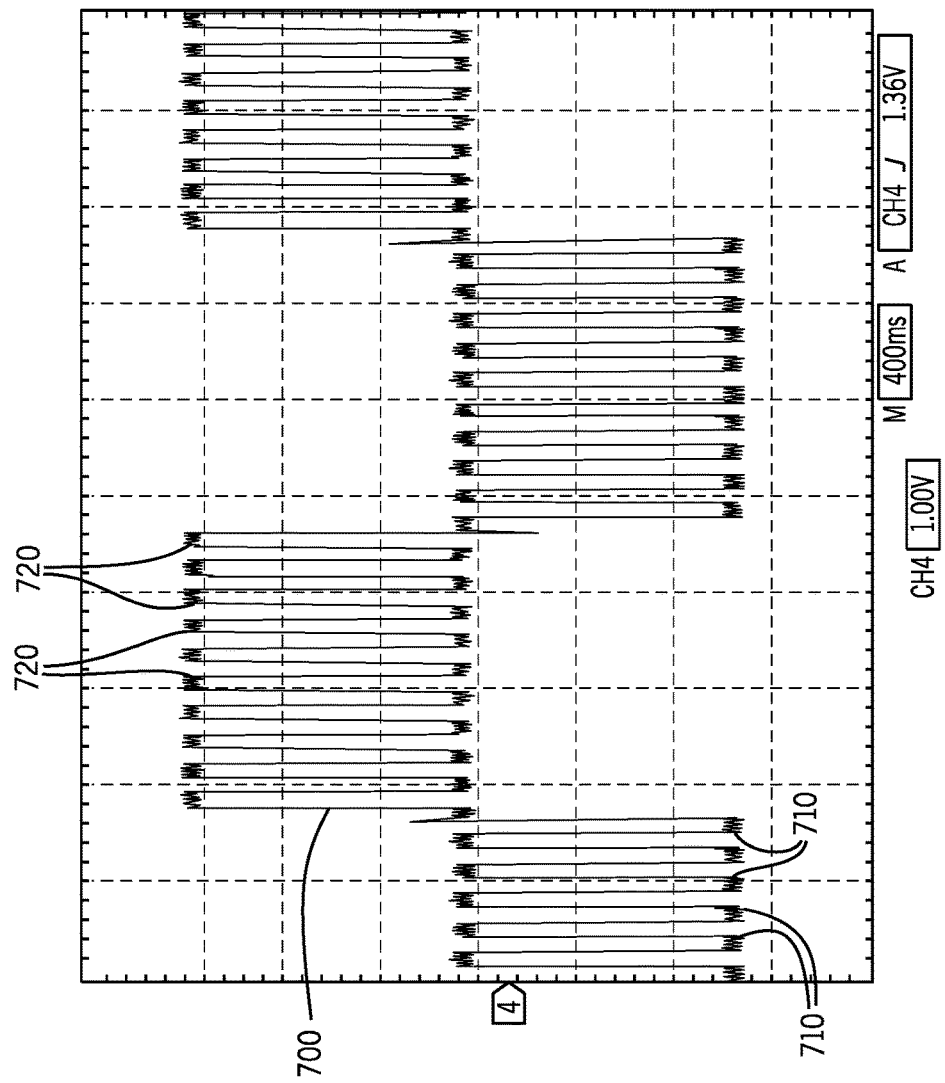
FIG. 7 shows a screenshot of an example TENS output signal waveform observed from the circuit subassembly of FIG. 6.

FIG. 7 shows a sample waveform output 700 from the circuitry of FIG. 6. As can be seen, the output consists of a sequence of pulses 710 of one polarity, followed by a similar sequence of pulses 720 of opposite polarity. This is a known aesthetic TENS waveform, approved for aesthetic TENS use by the FDA.

Based on tests of devices approved for aesthetic TENS in FDA filings, it appears that currents in the range from about 0.003 mA to about 0.700 mA (depending on the load resistance) and voltages from about 0.1 to about 6.0 V (again depending on the load resistance) are suitable for aesthetic TENS. The circuitry of FIG. 6 is programmable by programming the microprocessor 510. Accordingly, voltage and current levels and waveforms suitable for FDA approved TENS that are not specifically aesthetic TENS waveforms may also be produced by the circuitry of FIG. 6. Waveforms found to be therapeutic for skin by existing or future research may thus be implemented in the present device by suitable programming of microprocessor 510.

TENS Skin Contact Electrodes—Other Embodiments

Figure 11:
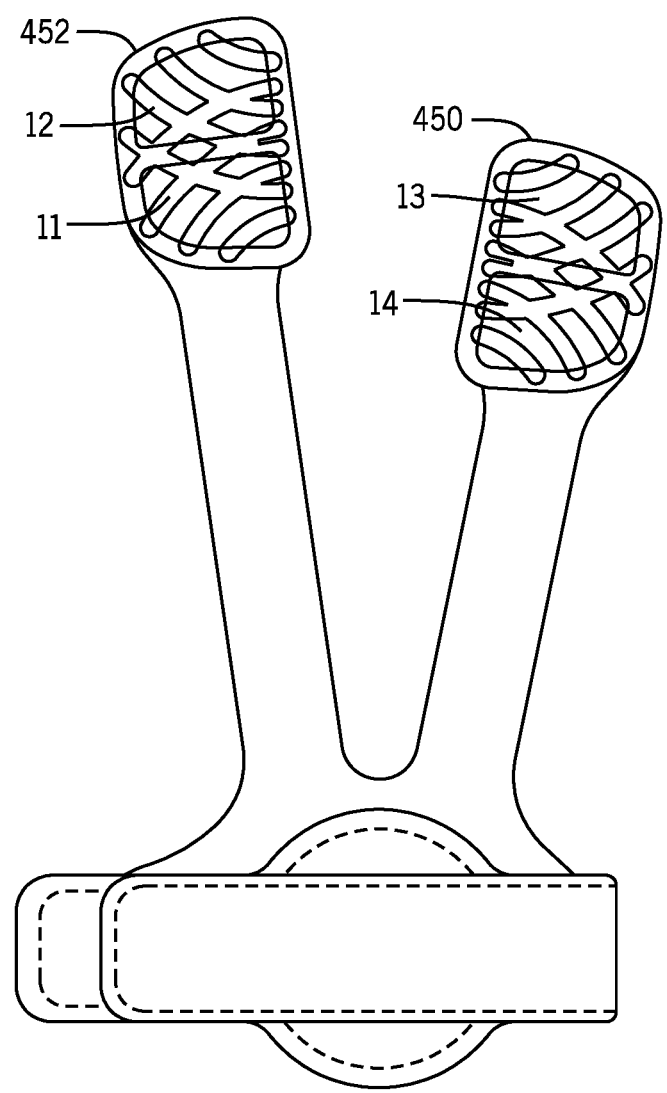
FIG. 11 is a pictorial bottom (palm side) view of the device of FIG. 10 in which an alternative embodiment of the fingertip electrodes is shown.

FIG. 11 shows an alternative embodiment for the configuration of the TENS fingertip electrodes relative to those in FIGS. 4A-4E. FIG. 11 shows a plan view of a device with two fingertip caps or attachment elements 450, 452 (such as those in FIG. 4A). Each fingertip cap or attachment element 450, 452 has two electrodes/contacts 11, 12 or 13, 14. The two electrodes are separated by a non-conducting area and one does not encircle the other. A variety of shapes can be used for electrodes/contacts beyond those in FIG. 11 or in other figures, involving both different shapes and, for electrode pairs, the shape of the surface area between two paired electrodes and the distance between the adjacent edges of the paired electrodes. For user comfort it has generally been found better to configure the electrodes with rounded corners (as seen in FIG. 11), because sharp corners tend to lead to current concentration and resulting possible user discomfort at a point or small area. In addition, maintaining a relatively constant distance between adjacent electrode edges, may also be helpful to avoid current concentration at particular points in the gap between adjacent, closely-spaced electrodes.

As can be seen in FIG. 11 the two, paired electrodes/contacts 11, 12 and 13, 14 may have a shallow surface pattern as indicated by the curving lines. This pattern may be selected primarily for visual appeal and may also have shallow channels between wider flat areas of the electrode surfaces that can assist in distributing lotion-type substances that may be used to improve conductivity with the skin, reduce friction that might impair user comfort or provide other skin benefits. It has been found that the use of conductive lotions between the skin-contacting electrodes and the skin may improve user comfort, because it assists in dispersing the current flow evenly and over a larger skin area. This reduces the chance of the current density at any point on the contacted skin being so high that it produces an unpleasant sensation.

Use of the Device: Spot or Wider Skin Treatment Area

As discussed above, a user of embodiments of the above-described device may select an operating mode, which involves selecting which electrodes are active. This mode selection, together with placement of the fingertips with active electrodes allows a user to direct the TENS current to desired treatment areas that are larger or smaller and are located at different parts of the face of other skin surface to be treated. In any mode involving active electrodes at two fingertips, the user can select the distance between the fingertips and define the endpoints of a treatment area. In any mode involving a single fingertip, the user can focus treatment on a small area, substantially defined by the surface area of an electrode pair and the area between them that is non-conductive. In embodiments of the device, the user also can select among a range of power levels. Accordingly, the user can select among multiple parameters to determine specific treatment areas, including areas limited substantially to the surface area of a pair of contact electrodes on one fingertip.

Various types of skin treatment and/or TENS conduction assisting compositions are useful in conjunction with the TENS treatment. In general, any liquid, dispersion, lotion, gel, serum, or solution conventionally used to improve conduction between skin and a TENS electrode can be used in conjunction with the TENS device During use, the TENS skin contact electrodes may be moved around the surface of the skin by the user and the TENS current flows through skin surfaces in conductive contact with electrodes. Examples of skin treatment or TENS conduction-assisting compositions usefully employed along with the TENS device include a Conductive Gel available from Nu Skin International, Inc. for use with a galvanic Facial Spa (Item 01003913).

While the device is intended to be used for cosmetic or aesthetic purposes, to the extent its use is found to provide any therapeutic effect, upon compliance with suitable testing and other regulatory requirements, the device might be used for situations other than cosmetic or aesthetic ones.

Summary

The invention illustratively disclosed herein can be suitably practiced in the absence of any element which is not specifically disclosed herein. While the invention is susceptible to various modifications and alternative forms, specifics thereof have been shown by way of examples, and are described in detail. It should be understood, however, that the invention is not limited to the particular embodiments described. On the contrary, the intention is to cover modifications, equivalents, and alternatives falling within the spirit and scope of the invention. In various embodiments, the invention suitably comprises, consists essentially of, or consists of the elements described herein and claimed according to the claims.

Additionally each and every embodiment of the invention, as described here, is intended to be used either alone or in combination with any other embodiment described herein as well as modifications, equivalents, and alternatives thereof falling within the spirit and scope of the invention. The various embodiments described above are provided by way of illustration only and should not be construed to limit the claims attached hereto. It will be recognized that various modifications and changes may be made without following the example embodiments and applications illustrated and described herein, and without departing from the true spirit and scope of the claims.

What is claimed is:

1. A device for delivery of electrostimulation:
   a first skin contact electrode, said skin contact electrode mounted on a first non-conductive fingertip base and comprising at least one contact area for current-bearing contact with skin and a connection to a TENS current source;
   a second skin contact electrode, said skin contact electrode mounted on a non-conductive fingertip base that is the same as the first non-conductive fingertip base or is a second non-conductive fingertip base and comprising at least one contact area for current-bearing contact with skin and a connection to TENS current source: and
   a control and power unit for supplying TENS current to flow through skin contacting and positioned between the first and second electrodes, and for selecting the level of the current or energy supplied, wherein the control and power unit is hand or wrist-mountable and at least one of the first and second nonconductive fingertip bases is connected to the control and power unit by a finger mounted link or leg comprising a flex sensor for sensing a degree of bending of the finger on which it is mounted and said device further comprises:
   a programmed processor communicating with the flex sensor and detecting the degree of bending; and
   a control module in the programmed processor responsive to the degree of bending for adjusting a user-selectable electrostimulation parameter according to the degree of bending.

2. The device of claim 1, wherein the control and power unit comprises:
   a controllable signal generator in the control and power unit for selecting an electrostimulation signal for delivery to a circuit comprising a skin area contacted by each of the first and second fingertip skin contact electrodes.

3. The device of claim 2, wherein the control and power unit selects the level of TENS current or energy supplied in response to a sensed impedance between the first and second fingertip mounted skin contact electrodes.

4. The device of claim 1, wherein
   the first skin contact electrode comprises at least two contact areas individually selectable for current-bearing contact with skin.

5. The device of claim 1, wherein:
   the second skin contact electrode comprises at least two contact areas individually selectable for current-bearing contact with skin.

6. The device of claim 1, wherein:
   the first skin contact electrode comprises at least two contact areas individually selectable for current-bearing contact with skin, with one contact area surrounding the other contact area.

7. The device of claim 1, wherein
   the first skin contact electrode comprises at least two contact areas individually selectable for current-bearing contact with skin, with one contact area being closely adjacent to the other contact area.

8. The device of claim 1, wherein the sensed degree of bending of a finger is used to determine whether an electrode on the finger with the flex sensor receives TENS current.

9. The device of claim 1, wherein the sensed degree of bending of a finger with a pair of electrodes is used to determine which one of two electrodes on the finger receives TENS current.

10. The device of claim 1 wherein the first skin contact electrode is in the form of a circle and the second skin contact electrode is in the form of a ring surrounding the circle, both electrodes being on one non-conductive fingertip base.

11. The device of claim 1 wherein each of the first and second skin contact electrodes is on one non-conductive fingertip base.

12. The device of claim 1, wherein the first skin contact electrode is on the first non-conductive fingertip base on a first finger and the second skin contact electrode is on the second non-conductive fingertip base on a second finger.

13. The device of claim 1, further comprising at least one sensor communicating with the control and power unit for sensing one of the following: impedance between the first and second fingertip mounted skin contact electrodes, skin moisture or skin temperature.

14. The device of claim 1 further comprising a computer-based current recommendation module in the control and power unit for taking as input one or more of a sensed value for impedance between the first and second skin contact electrodes, skin moisture or skin temperature and providing as output a recommended output current for providing a TENS signal for delivery to a circuit comprising a skin area contacted by each of the first and second skin contact electrodes via first and second electrical connections to the control and power unit.

15. The device of claim 1, further comprising a controllable signal generator wherein a user can select by a user input interface a current level for the current to flow through skin contacting and positioned between the first and second electrodes.

16. The device of claim 1 wherein:
   the first skin contact comprises at least two contact areas individually selectable for current-bearing contact with skin; and
   the second skin contact electrode comprises at least two contact areas individually selectable for current-bearing contact with skin.

17. A method for delivery of electrostimulation, comprising:
providing:
a first skin contact electrode, said skin contact electrode mounted on a first non-conductive fingertip base and comprising at least one contact area for current-bearing contact with skin and a connection to a TENS current; and
a second skin contact electrode, said skin contact electrode mounted on a non-conductive fingertip base that is the same as the first non-conductive fingertip base or is a second non-conductive fingertip base and comprising at least one contact area for current-bearing contact with skin and a connection to a TENS current; and
a control and power unit for providing a TENS current, wherein the control and power unit is hand or wrist-mountable and at least one of the first and second nonconductive fingertip bases is connected to the control and power unit by a finger mounted link or leg comprising a flex sensor for sensing a degree of bending of the finger on which it is mounted and said method further comprises;
with a programmed processor communicating with the flex sensor and detecting the degree of bending; and
with a control module in the programmed processor responsive to the degree of bending, adjusting a user-selectable electrostimulation parameter according to the degree of bending.

18. The method of claim 17, further comprising:
with the control and power unit for providing a TENS current, accepting a user input representing selection of
(a) providing a current between the first skin contact electrode and the second skin contact electrode both mounted on the first non-conductive fingertip base or
(b) providing a current between the first skin contact electrode, mounted on the first non-conductive fingertip base and the second skin contact electrode mounted on the second non-conductive fingertip base.

19. The method of claim 17, further comprising with the control and power unit for providing a TENS current, accepting a user input representing selection of a distance between the first skin contact electrode and the second skin contact electrode.

20. The method of claim 17, further comprising;
sensing with at least one sensor communicating with the control and power unit one of the following: impedance between the first and second fingertip mounted skin contact electrodes, skin moisture or skin temperature; and
selecting a level of TENS current or energy supplied between the electrodes in response to a sensed value of impedance between the first and second fingertip mounted skin contact electrodes, skin moisture or skin temperature.

* * * * *